United States Patent
Nagy

(10) Patent No.: US 12,097,347 B2
(45) Date of Patent: Sep. 24, 2024

(54) SYSTEM AND METHOD FOR A SHUNT

(71) Applicant: Medtronic Xomed, Inc., Jacksonville, FL (US)

(72) Inventor: Elizabeth K. Nagy, Maple Grove, MN (US)

(73) Assignee: Medtronic Xomed, Inc., Jacksonville, FL (US)

( * ) Notice: Subject to any disclaimer, the term of this patent is extended or adjusted under 35 U.S.C. 154(b) by 409 days.

(21) Appl. No.: 17/080,368

(22) Filed: Oct. 26, 2020

(65) Prior Publication Data
US 2022/0126073 A1 Apr. 28, 2022

(51) Int. Cl.
*A61M 27/00* (2006.01)
*A61M 25/00* (2006.01)

(52) U.S. Cl.
CPC ...... *A61M 27/006* (2013.01); *A61M 25/0026* (2013.01); *A61M 2025/0078* (2013.01); *A61M 2205/0266* (2013.01); *A61M 2210/0693* (2013.01)

(58) Field of Classification Search
CPC ............ A61M 27/006; A61M 25/0026; A61M 2025/0078; A61M 2205/0266; A61M 2210/0693; A61M 2025/0293; A61M 25/04; A61M 25/10; A61M 2210/0687; A61M 2202/0464; A61B 2017/00986; A61B 2017/00991
See application file for complete search history.

(56) References Cited

U.S. PATENT DOCUMENTS

| | | | | |
|---|---|---|---|---|
| 5,267,960 | A * | 12/1993 | Hayman | A61N 5/1027 600/3 |
| 5,282,845 | A * | 2/1994 | Bush | A61N 1/0587 607/128 |
| 5,509,900 | A * | 4/1996 | Kirkman | A61M 25/04 606/198 |
| 6,050,992 | A * | 4/2000 | Nichols | A61B 18/1477 606/49 |
| 6,077,282 | A * | 6/2000 | Shturman | F16D 43/14 606/159 |
| 6,188,932 | B1 * | 2/2001 | Lindegren | A61N 1/057 607/126 |
| 6,358,258 | B1 * | 3/2002 | Arcia | A61B 17/0469 606/139 |
| 6,684,109 | B1 * | 1/2004 | Osypka | A61N 1/0573 607/122 |
| 9,775,982 | B2 | 10/2017 | Grubac et al. | |

(Continued)

FOREIGN PATENT DOCUMENTS

CN 103189009 A * 7/2013 ....... A61B 17/00234

OTHER PUBLICATIONS

"The Future is Here," Micra AV product brochure, Medtronic, 12 pages, 2020.

*Primary Examiner* — Adam Marcetich
(74) *Attorney, Agent, or Firm* — Harness, Dickey & Pierce, P.L.C.

(57) ABSTRACT

Disclosed is a system including a flow regulating system. The flow regulating system may assist in ensuring a selected pressure within an inlet volume. The flow regulator may be included in a shunt assembly. The shut assembly may include an inlet catheter configured to assist in maintaining an open flow path therethrough.

21 Claims, 5 Drawing Sheets

(56) References Cited

U.S. PATENT DOCUMENTS

| | | | | |
|---|---|---|---|---|
| 2003/0009191 A1* | 1/2003 | Wensel | ............... | A61B 17/221 606/200 |
| 2005/0101982 A1* | 5/2005 | Ravenscroft | ..... | A61B 17/12109 606/182 |
| 2005/0288722 A1* | 12/2005 | Eigler | ................. | A61M 31/002 607/9 |
| 2008/0215085 A1* | 9/2008 | Whisenant | ........ | A61B 18/1492 606/213 |
| 2008/0228209 A1* | 9/2008 | DeMello | ......... | A61B 17/32056 606/159 |
| 2009/0264903 A1* | 10/2009 | Lee | ..................... | A61B 17/068 606/151 |
| 2011/0251660 A1* | 10/2011 | Griswold | ........... | A61N 1/37205 607/126 |
| 2012/0172892 A1* | 7/2012 | Grubac | ................... | A61N 1/05 606/129 |
| 2012/0184977 A1* | 7/2012 | Wolf | ................... | A61B 17/221 606/159 |
| 2013/0253275 A1* | 9/2013 | Ransden | ........... | A61B 17/0401 600/204 |
| 2014/0257248 A1* | 9/2014 | Millett | ................. | A61M 25/04 604/528 |
| 2014/0303637 A1* | 10/2014 | Downer | ............ | A61B 17/3468 606/107 |
| 2014/0350593 A1* | 11/2014 | Laroya | .................... | A61F 2/011 606/200 |
| 2015/0051613 A1* | 2/2015 | Schmidt | ............... | A61N 1/3756 606/129 |
| 2015/0157268 A1* | 6/2015 | Winshtein | ........... | A61B 5/6882 600/300 |
| 2015/0196741 A1* | 7/2015 | Heilman | ................ | A61B 90/39 604/9 |
| 2015/0343199 A1* | 12/2015 | Wechter | .............. | A61N 1/0558 607/116 |
| 2016/0015394 A1* | 1/2016 | Cedro, Jr. | ........ | A61B 17/12131 606/139 |
| 2016/0143721 A1* | 5/2016 | Rosenbluth | .... | A61B 17/320725 600/200 |
| 2016/0287276 A1* | 10/2016 | Cox | ...................... | A61M 25/01 |
| 2016/0310723 A1* | 10/2016 | Eggen | ................. | A61N 1/3756 |
| 2018/0028790 A1* | 2/2018 | Bar-Cohen | ......... | A61N 1/37205 |
| 2018/0220992 A1* | 8/2018 | Gifford, III | ............ | A61B 8/06 |
| 2018/0353754 A1* | 12/2018 | Momma | ............. | A61N 1/3756 |
| 2019/0083800 A1* | 3/2019 | Yang | ..................... | A61N 1/368 |
| 2019/0328420 A1* | 10/2019 | Khairkhahan | ..... | A61B 17/3417 |

\* cited by examiner

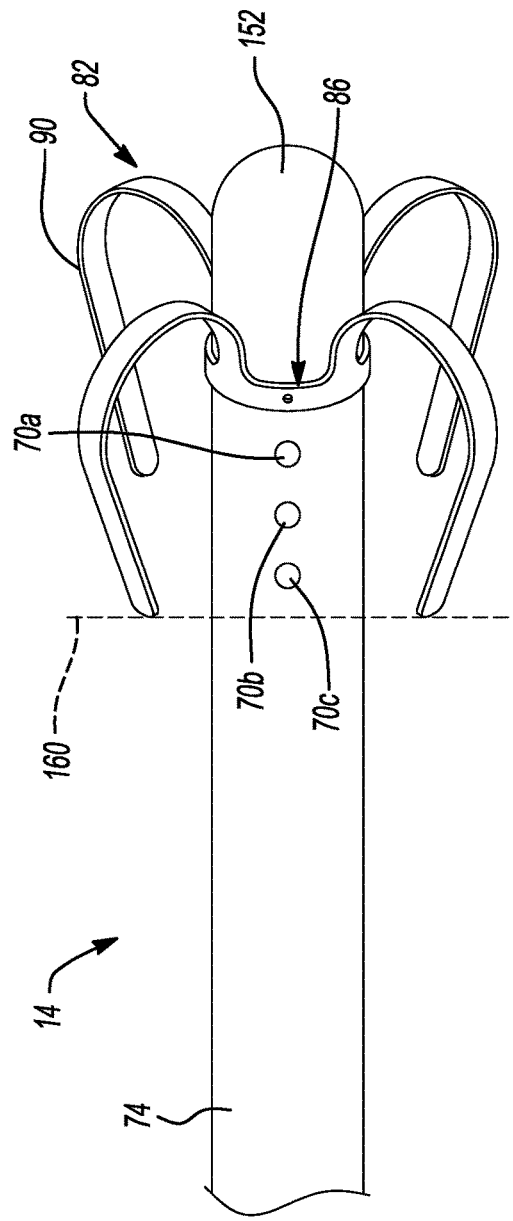
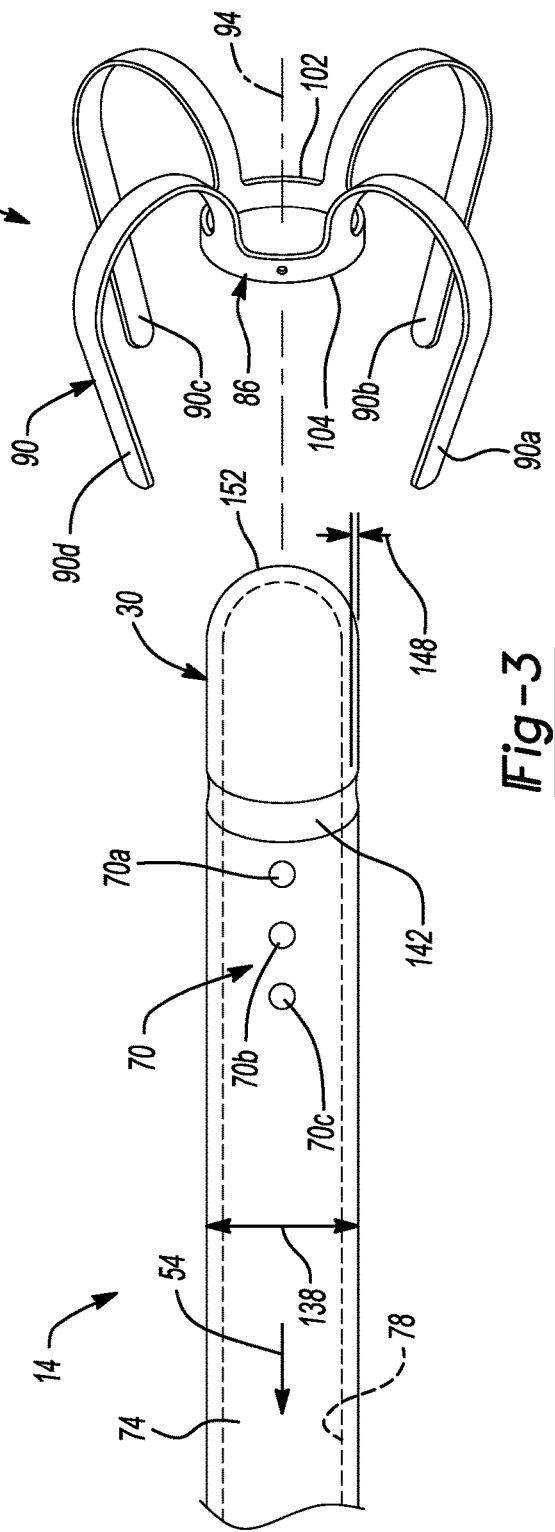

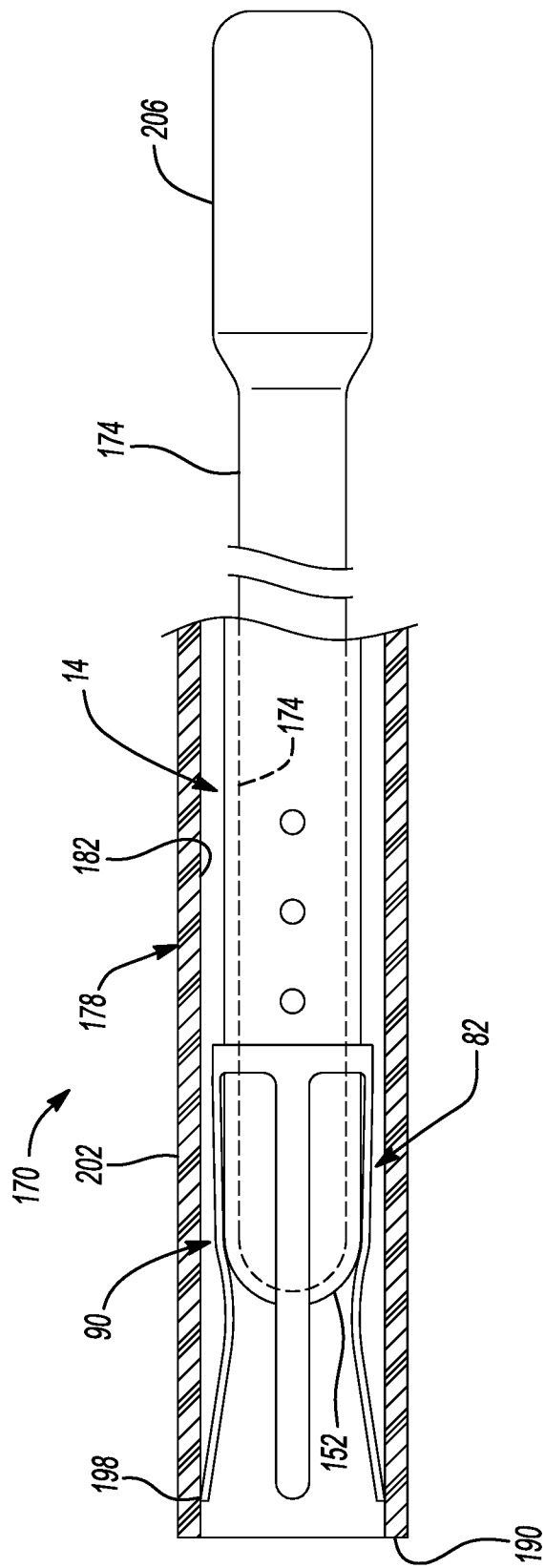

SYSTEM AND METHOD FOR A SHUNT

FIELD

The subject disclosure relates to a valve, and particularly to a valve assembly having an inlet and outlet catheter.

BACKGROUND

This section provides background information related to the present disclosure which is not necessarily prior art.

A subject, such as a human patient, may have a condition for which a treatment may be prescribed. For example, hydrocephalous may generally include an overproduction of cerebral fluid in the ventricles of the brain and/or an abnormal absorption or outflow of cerebral fluid from the brain. The condition, therefore, may cause an inappropriate or undesirable increase in volume of cerebral spinal fluid (CSF) within the ventricles in the brain and an increased pressure on the brain within the skull.

In various instances, a shunt may be implanted into the subject. The shunt may include an inflow catheter positioned within a ventricle of the brain and an outflow catheter positioned at a location remote from the brain. The excess cerebral spinal fluid may, therefore, flow from the ventricle to a selected location in the subject. The flow of the CSF from the ventricle through the inflow and outflow catheters may allow for an appropriate or selected volume of CSF within the brain to achieve a selected pressure on the brain within the skull. Maintaining a selected pressure within the ventricles, however, is desired.

SUMMARY

This section provides a general summary of the disclosure, and is not a comprehensive disclosure of its full scope or all of its features.

A catheter may be positioned in a selected portion of a subject, such as within a ventricle of a brain of a human subject. The catheter may include passages, such as bores, through a selected portion of a catheter. The catheter may further include an internal cannula or passage to allow flow of a selected material, such as a liquid, therethrough. In various embodiments, the catheter may allow for flow of cerebral spinal fluid (CSF). The catheter may be implanted as a part of a shunt system to shunt or drain CSF from a first location to a second location.

The shunt assembly may include the catheter positioned within the ventricle of the brain and a catheter positioned at a location remote from the ventricle of the brain. Positioned between the ventricle and the remote location may be a flow regulating system. The flow regulating system may include a valve assembly that is positioned in line with the catheters. The valve assembly may be used to regulate or select a pressure to be maintained within the ventricle.

In various embodiments, the valve assembly may include an opening or breaking pressure. The breaking pressure would need to be achieved and/or exceeded to open the valve and allow fluid flow through the valve. The valve assembly may include various portions that allow for variation of the inlet pressure prior to opening the valve, as discussed further herein. The valve assembly, therefore, may be used to maintain a selected volume and/or a pressure in a ventricle.

The catheters may include openings or passages. Further, the catheters may generally be placed near or adjacent tissue in the subject. The catheters may, therefore, include members, such as projections, to locate tissue or surfaces a selected distance from the openings or passages of the catheter. The openings or passages, when open, allow for efficient and selected operation of the shunt assembly. Blockages of the catheters may limit the operation of the shunt assembly.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is an elevational view of a catheter, according to various embodiments;

FIG. 3 is an exploded view of the catheter assembly of FIG. 2;

FIG. 4 is a detail partial cross-sectional view of a catheter and an introducer assembly;

Corresponding reference numerals indicate corresponding parts throughout the several views of the drawings.

DETAILED DESCRIPTION

Example embodiments will now be described more fully with reference to the accompanying drawings.

Figure 1:
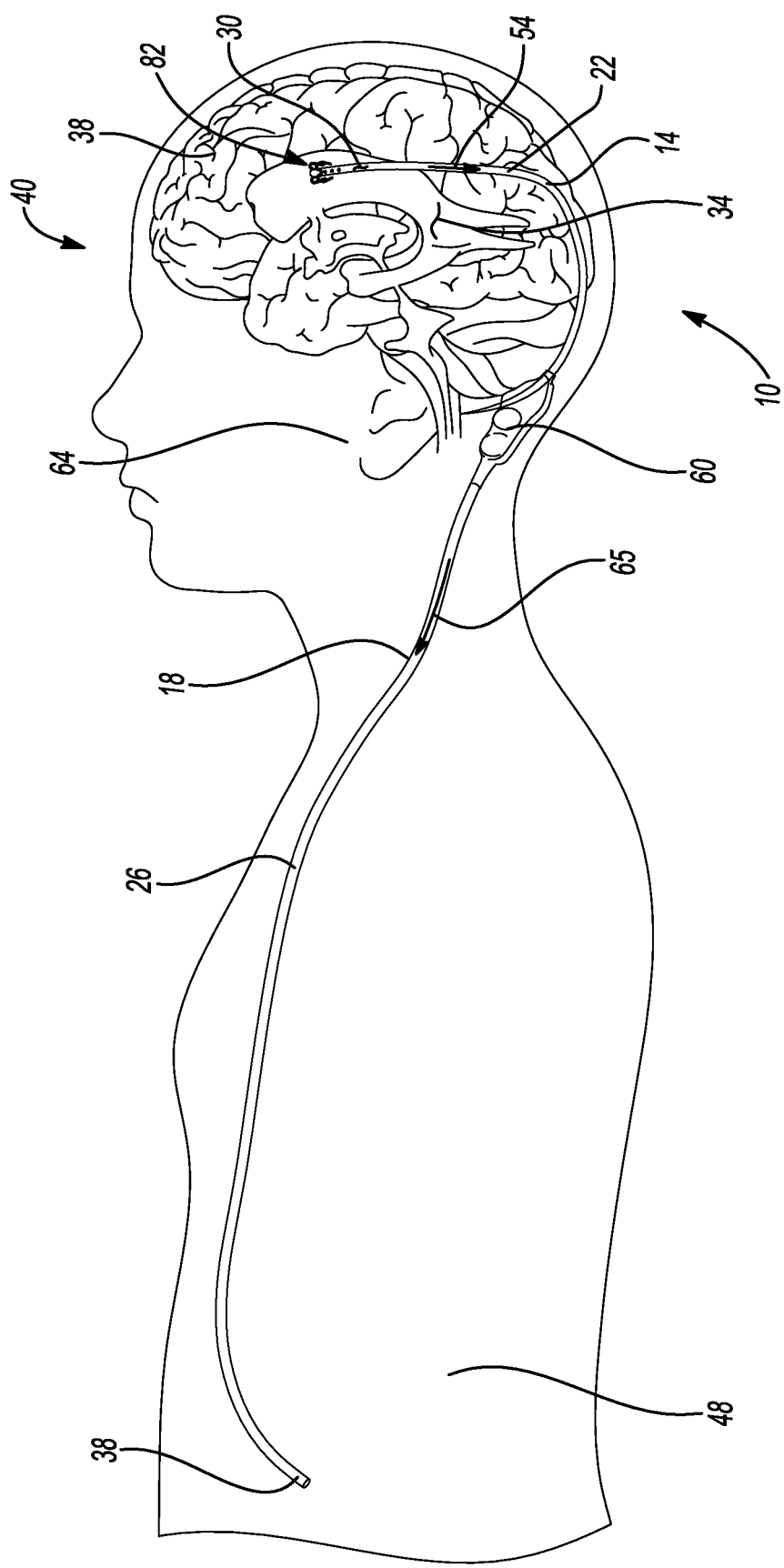
FIG. 1 is an environmental schematic view of a shunt and system positioned in a subject, according to various embodiments.

With initial reference to FIG. 1, a shunt system 10 is illustrated. The shunt system may include an inlet or first catheter 14 and an outlet or second catheter 18. The catheters, 14, 18 includes a member or wall structure that includes or defines an exterior surface 22, 26. The catheters 14, 18 may include a selected length or be formed along a long or longitudinal axis. In various embodiments, the catheter 14 may be provided as an inflow or inlet catheter or portion for the shunt assembly 10 as a hydrocephalous shunt. The hydrocephalous shunt may be configured, such as formed, assembled, and/or implanted to shunt cerebral spinal fluid (CSF) from a position near a first or inlet portion 30 of the catheter 14 in a ventricle 34 in a brain 38 of a subject 40 to a second or distal end 42 at a position remote or away from the inlet end or portion 30. The second or outlet end 38 may be in a selected portion of the subject 40, such as a peritoneum 48.

A fluid, such as a cerebral spinal fluid (CSF) may flow along the catheter 22 from the ventricle 34 generally in the direction of arrow 50 toward the outlet end 38. As is generally understood by one skilled in the art, the inlet catheter 22 may be positioned (i.e. implanted) in the ventricle 34 to allow the fluid to be drained away from the ventricle 34. The inlet catheter 22 may be a part of the shunt system 10 that includes a selected flow control system, such as a valve assembly 60, according to various embodiments, as discussed further herein.

While the shunt assembly 10 is illustrated in a human subject, such a requirement need not be included with the subject disclosure. The shunt assembly 10 may be included in a non-human living subject. Further, the shunt assembly 10 may be included in a non-living subject. For example, the shunt assembly 10 may be used to shunt or move liquid from a first container to a second container, such as a fuel supply to a vehicle engine or reserve tank, when emptying a tank (e.g., an aquarium), etc.

In various embodiments, the valve assembly 60 may be implanted in the subject 40 in an appropriate position. In various embodiments, the valve assembly 60 may be implanted generally subdermal near an ear 64 of the subject 40, or any other appropriate location. It is understood that the inlet catheter 22 may be connected to the valve assembly 60. Thus, the inlet catheter 22 and the valve assembly 60 may both be implanted in the subject 40.

The subject disclosure includes an exemplary application for draining CSF in a subject. It is understood, however, that the valve assembly 60, according to various embodiments and/or portions thereof, may be used or implemented for alternative uses. For example, draining a selected fluid in any appropriate portion of a subject. Further, subjects may be living or non-living. For example, the valve assembly may be used for controlling flow or pressure from a first tank to a second tank or drain.

The valve assembly 60 may be further connected to the outlet catheter 26. The outlet catheter 26 may extend from the valve assembly 60 to a selected location, such as the peritoneal cavity 48 of the subject 40. The inlet catheter 22, the valve assembly 60, and the outlet catheter 26 may generally be understood to be the shunt system 10, such as a hydrocephalus shunt system. The shunt system 10 may be entirely implanted in the subject 40.

The fluid may flow in the direction of arrow 54 through the inlet catheter 22 to the valve assembly 60. The fluid may then flow through the valve assembly 60 and through the outlet catheter 26 generally in the direction of arrow 65. The fluid may then drain or pass through the outlet catheter 26 into a peritoneal cavity 48, or any other appropriate location of the subject 40. It is understood that the outlet catheter 26 may be positioned within the subject 40 in an appropriate location to allow for draining of the CSF from the ventricle 34 to an appropriate location, such as one with high blood flow. Accordingly, as illustrated in FIG. 1, the inlet catheter 22, the valve assembly 60 and the outlet catheter 26 may be implanted or positioned in the subject 40 as a CSF shunt system.

With continuing reference to FIG. 1 and with additional reference to FIG. 2 and FIG. 3, the inlet catheter 14 will be described in greater detail. The inlet catheter 14 may include one or more inlet passages that may be provided in an appropriate shape (e.g., round, elongated, slit, etc.), size, or configuration. The inlet passages that may also be referred to as bores, holes, or through-bores 70 at or near the inlet end 30. In various embodiments, for example, the inlet bores may include a first inlet bore 70a, a second inlet bore 70b, a third inlet bore 70c, and a fourth inlet bore 70d. It is understood, however, that a plurality or selected number of the inlet bores 70 may be provided in the inlet catheter 14. The bores 70 may also be provided in an appropriate configuration. For example, each of the bores 70a, 70b, 70c may include two or more bores that are formed around the catheter 14, such as in a ring or row. Thus, a plurality of rows or rings of the bores 70 may be provided.

The inlet through-bores 70 may be formed through a wall 74 of the inlet catheter 14. The wall 74 may be formed around a cannula or internal passage 78 of the catheter 14. Thus, the bores 70 may be formed from an exterior of the wall 74 to the cannula or passage 78 and may allow the flow of a fluid (e.g., CSF) through the inlet bores 70 and through the cannula or passage 78 generally in the direction of arrow 54. Thus, as discussed further herein, fluid may flow through the inlet bores 70 into the internal passage 78 and through the inlet catheter 14. Further, in the shunt system 10, fluid may flow through the inlet catheter 14, such as though the bores 70, through the valve assembly 60, and, then, through the outlet catheter 26.

The shunt system 10 may further include a spacer member 82. The spacer member 82 may be configured in a selected orientation or configuration to maintain a distance of tissue from the inlet bores 70. In various embodiments, as discussed further herein, the inlet catheter 14 may be positioned in the ventricle 34 of the subject. The spacer or maintaining member 82 may be positioned relative to the inlet catheter 14 to assist in maintaining a position or distance of tissue relative to the inlet bores 70 of the inlet catheter 14.

Figure 3A:
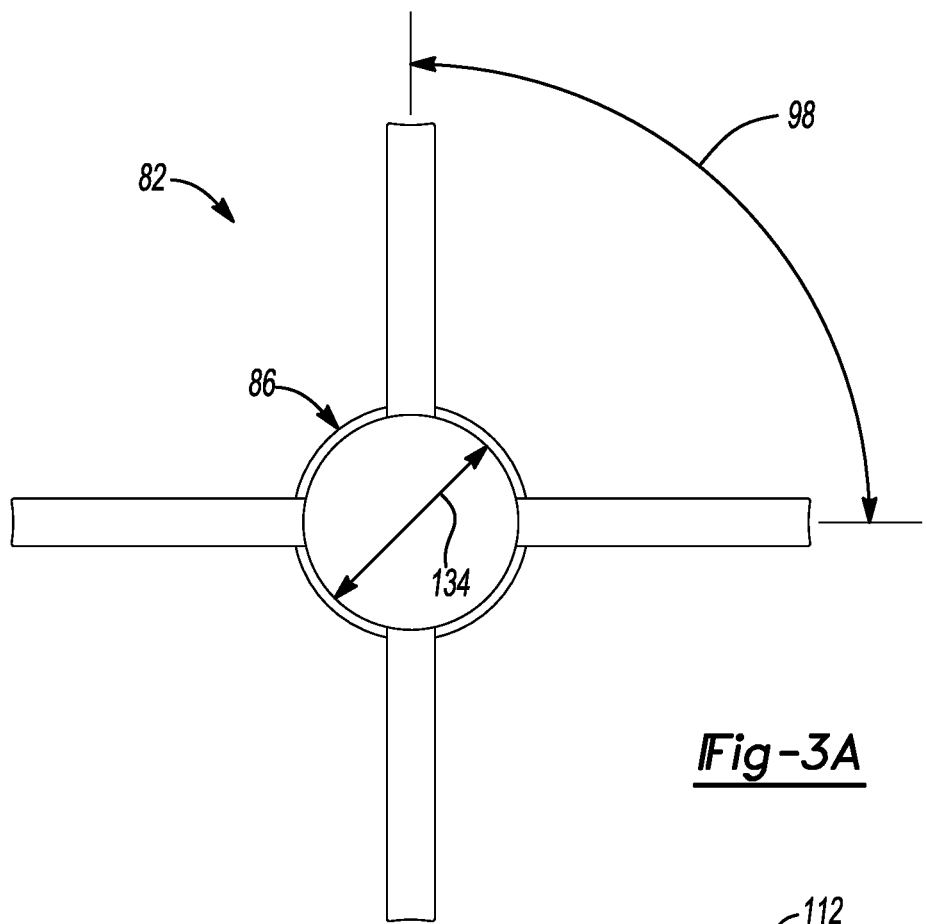
FIG. 3A is a side elevational view of a spacing member, according to various embodiments.
Figure 3B:
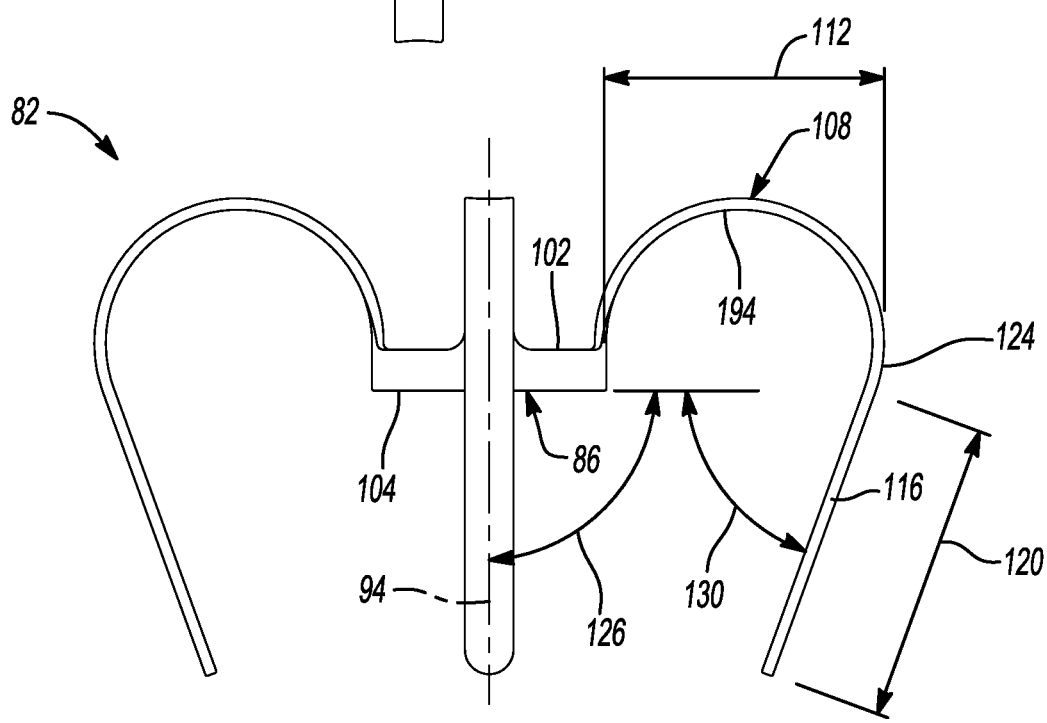
FIG. 3B is a top elevational view of the space member of FIG. 3A.

The maintaining member 82 may also be referred to as a spacer or spacing member to assist in spacing or positioning tissue away from the inlet catheter 30. With continuing reference to FIG. 3, the spacer member 82 may generally include a central ring or catheter engaging portion 86 and one or more spacing portion or projection 90. The projection 90 may also be referred to as a tine or finger. In various embodiments, for example, the spacing member 82 may include four spacing portions 90 designated as 90a, 90b, 90c, and 90d. With continuing reference to FIG. 3, and additional reference to FIGS. 3A and 3B, the spacer member 82 will be described in further detail.

The spacer member 82, including the selected plurality of projection portions 90, may include the four projection portions 90a-90d. In various embodiments, therefore, the projections may be positioned around a central axis or portion 94 of the spacer member 82 at an angle 98. The angle 98 may be a selected angle such as about 60° to about 120°, including about 90°. Accordingly, each of the four projection portions 90 may be substantially equally spaced around the central axis 94.

Each of the projections 90 may extend in a first direction, such as away from a top portion 102 of the central ring 86. The central ring 86, therefore, may also include a bottom or second side 104. Generally, the projections 90 may extend along an arc or curve in a first curved or arcuate portion 108. The arcuate portion 108 may generally have a selected radius, such as a radius of about 0.4 inches to a radius of about 1 inch, and further including a radius of about 0.6 inches to about 0.7 inches. The arcuate portion 108 may further extend a selected distance 112 from the central ring 86. The distance 112 may be any selected distance such as about 0.01 inches to about 0.2 inches, and further including about 0.12 inches to about 0.15 inches. The projections 90 may also include a substantially straight or planar portion 116. The planar portion 116 may extend from the curved portion 108 a selected distance 120. The distance 120 may be about 0.1 inches to about 0.2 inches including about 0.14 to about 0.16 inches. A transition area 124 may be formed between the curved or arcuate portion 108 and the substantially planar portion 102.

Accordingly, as illustrated in FIG. 3A the projections may have a selected angle 126 relative to the bottom surface 104 of the ring 86. The angle 126 may be about 70° to about 120°, including about 90°. The substantially straight portion 116 may also include an angle 130 from the bottom surface 104. The angle 130 may generally be less than about 90° including about 30° to about 85°, and further including about 70°.

The central ring 86 may generally include a central or internal diameter 134 that may be formed to engage or be fixed relative to the inlet catheter 14. In various embodiments, for example, the internal diameter 134 may be substantially equivalent to an external diameter 138 of the inlet catheter 14. In various embodiments, however, the inlet catheter 14 may also include a groove or depression 142 that may extend around at least a portion of an outer diameter or outer geometry of the inlet catheter 14, such as formed in the wall 14. The groove 142 may include a depth or distance 148 from the external surface 74. The depth 148 of the groove 142 may be any appropriate depth that may allow for the external surface of the ring 86 to be substantially flush with the external surface 74 of the inlet catheter 14 and/or any appropriate distance therefrom. The groove 142 may assist in holding or fixing the spacing member 82 relative to the inlet catheter 14, such as relative to a distal terminal end 152 of the inlet catheter 14.

In various embodiments, for example, the spacing member 82 may be fixed relative to the inlet catheter 14 with a selective adhesive, bonding procedure, or other appropriate mechanism. For example, the spacing member 82 may be solvent bonded to the wall 74 of the inlet catheter 14. In various embodiments, for example, the spacing member 82 may be positioned in the groove 142 and be frictionally held or biased in the groove 142 by the size of the ring 86 and a selected elastic movement of the wall 74 of the inlet catheter 14. In addition, and/or alternatively thereto, the ring 86 of the spacing member 82 may be bonded in the groove 142, such as with a selected adhesive. The spacing member 82 may, however, also be formed as a single piece with the catheter 14. The spacer member, for example, may be formed during an injection molding, extrusion, or additive manufacturing process.

In various embodiments, the spacer member 82 may be formed as a single piece separate from the catheter 14. Further, the spacer member 82 may be formed of a plurality of members that are then fixed together in an integrated member. The spacer member 82 may be formed of a selected material. Selected materials may include elastically deformable materials, particularly materials that have a memory. In various embodiments, the spacer member 82 is formed of a memory alloy such as nitinol or other selected nickel titanium alloys. Generally, the memory alloy may be formed or placed in selected configuration and will return to the selected configuration after being deformed therefrom.

With continuing reference to FIGS. 2-3B, and with particular reference to FIG. 2, the projections 90 may extend from the ring 86 toward a proximal end, such as away from the terminal end 152, of the catheter 14. The catheter 14, as discussed above, can include a plurality of the through-bores 70. The projections 90 may extend a selected distance, such as to a point or plane 160 such that a selected number of the through-bores 70 are overlaid by the projections 90. For example, as illustrated in FIG. 2, the projections 90 may extend over at least two of the through-bores 70a, 70b and to a third through bore 70c. The projections 90, as discussed herein, form a barrier relative to the through-bores 70.

It is understood, however, that the projections 90 may extend to any appropriate position relative to the terminal end 152 of the catheter 14 to assist in maintaining a position of tissue relative to the through-bores 70, as discussed further in. The projections 90, however, may extend a selected distance to assist in ease or efficiency of implantation or positioning of a catheter 14, ease or efficiency of revision removal of the catheter 14, or other appropriate considerations. For example, including the projections 90 at a length that extends over a greater number of the through-bores 70 may increase a mass of the spacer member 82 and reduce efficiency of, for example, revision of the catheter 14.

Figure 5:
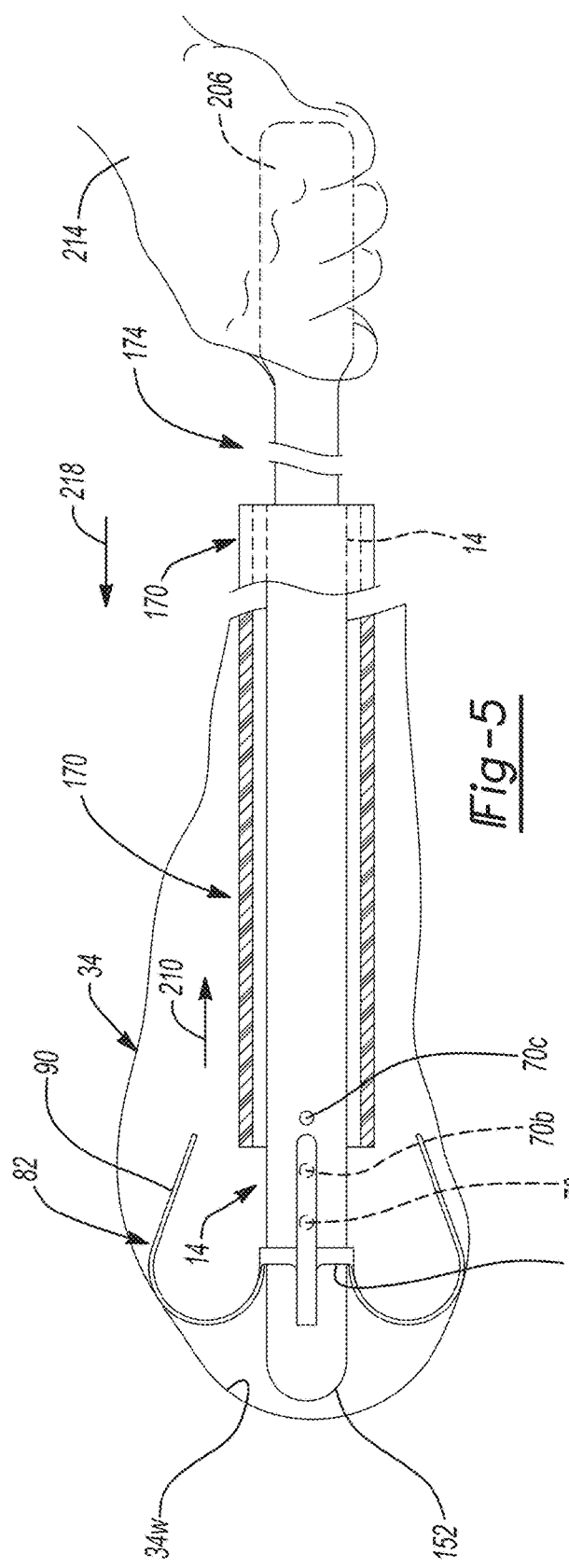
FIG. 5 is an environmental view of an insertion of a catheter assembly, according to various embodiments.

With continuing reference to FIGS. 1A-3B, and further reference to FIGS. 4 and 5, the catheter 14 may be positioned in the ventricle 34 of the subject. The catheter 14 may be positioned in the ventricle 34 in any appropriate manner, such as discussed further herein, including a first insertion or placement member that may also be referred to as an introducer 170. In various embodiments, the catheter 14 may further be positioned into the subject 40, such as in the ventricle 34, with the use or assistance of a second insertion member also referred to as a stylet or mandrel 174.

With particular reference to FIG. 4, the introducer 170 may be formed of a selected material, such as a substantially rigid polymer. The material of the introducer 170 may be formed of a biocompatible material to assist in positioning the catheter 14 within the subject 40. The introducer 170 may include an external wall 178 that may define an internal surface 182. The internal surface may be formed to assist in engaging the projections 90 in a selected manner. For example, the introducer 174 may be moved along the catheter 14 generally in the direction of arrow 186. As the introducer 170 moves in the direction 186 a terminal end 190 may engage a portion of the spacer member 82, such as generally at an internal edge or surface 194 of each of the projections 90. As the introducer 170 continues to move in the direction of arrow 186 relative to the catheter 14, the projections 90 may extend from a non-extended (e.g., curled, curved, or compact) position, is illustrated in FIGS. 3A and 3B, to an extended or elongated orientation, as illustrated in FIG. 4. In the extended orientation, as illustrated in FIG. 4, the projection 90 may extend past the terminal end 152 of the catheter 14. Further, a terminal end or other appropriate portion, based upon the geometry of the projections 90, may engage the internal surface 182 of the introducer 170. As illustrated in FIG. 4, an end or a portion near an end 198 of the projections 90 may engage the inner surface 182 of the introducer 170.

As illustrated in FIG. 4, therefore, the catheter 14 including the spacer member 82 may be received a selected amount, such as entirely, within the introducer 170. In this configuration, the introducer 170, including the outer wall 178 that may have an outer wall surface 202, may be moved through the ventricle 34 of the subject 40 within the catheter 14 therein. The outer wall surface 202 may be substantially smooth and free of obstructions or projections to assist in insertion of the introducer 170 including the catheter 14 into the ventricle 34. Further, the external surface 202 may include a selected lubrication material to assist insertion of the introducer 170 with the catheter 14 into the ventricle 34. Also, the stylet 174 may be axially inserted through at least a portion of the catheter 14 to assist in positioning or moving the catheter 14 within the subject 40. The stylet 174 may include a grasping portion 206 (e.g., handle portion, ring, etc.) to assist in using the stylet 174.

With continuing reference to FIGS. 1-4 and additional reference to FIG. 5, the catheter 14 may then be positioned into the ventricle 34 at a selected location. Once the introducer 170 has moved to the catheter 14 to a selected position (e.g., so that the catheter 14 will be operational for a selected purpose, such draining of a CSF) the catheter 14 may be positioned such as by generally moving the introducer 170 generally axially in the direction of arrow 210. In various embodiments, the terminal end 152 of the catheter 14 may be positioned at or near an internal wall 34*w* of the ventricle 34. It is understood, however, that the catheter 14 may be positioned in any appropriate location. Further the stylet 174 may be engaged, such as by a hand of a user 214. The stylet 174 may engage near a terminal end 152 of the catheter 14 to resist movement of the catheter 14 in the direction of arrow 210 as the introducer 170 is withdrawn and/or pushed in a direction of arrow 218 to assist in removing the catheter 14 from the introducer 170.

Accordingly, as illustrated and discussed above, the introducer 170 may be used to position or assist in positioning the catheter 14 within the ventricle 34. Once the catheter 14 is positioned in the ventricle 34 the introducer 170 may be withdrawn from the catheter 14 and the ventricle 34. The stylet or mandrel 174 may assist in removing the introducer 170 from the catheter 14 such as by maintaining or holding the catheter 14 in a position and/or pushing the catheter 14 out of the introducer 170.

The introducer 170, therefore, may be used to move the projections 90 to the extended configuration during insertion of the catheter 14. The introducer 170 may hold the projections 90 in the extended configuration. Once the catheter has reached a selected position, the introducer 170 may be withdrawn. By withdrawing the introducer 170, the projections 90 may return to the pre-insertion configuration which may also be referred to as the barrier configuration. Thus, the projections 90 may be elastically deformed such that they return to the selected configuration or position.

Figure 6:
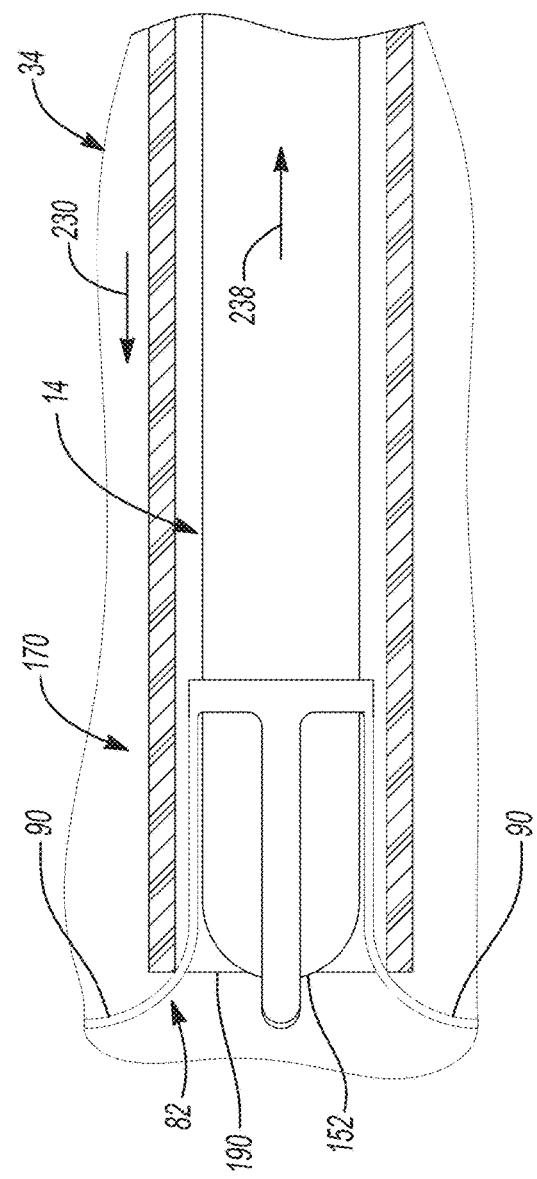
FIG. 6 is an environmental view of a revision procedure of a catheter assembly, according to various embodiments.

With continuing reference to FIGS. 1-5 and additional reference to FIG. 6, in various embodiments, the catheter 14 may be removed from the ventricle 34, for various purposes. For example, the patient 40 may require and/or have selected an alternative treatment. Further, in various embodiments, the size of the catheter 14 may need to be altered as the subject 40 changes in size and/or volume. Nevertheless, the catheter 14 may be selected to be removed from the subject 40.

As illustrated in FIG. 6, the introducer 170, or any appropriate removal member, may be moved generally in the direction of an arrow 230. The introducer 170 may generally move in the direction of arrow 230 over the catheter 14 to engage the projections 90 of the spacer 82. For example, as discussed above, the terminal end 190 of the introducer 170 may engage a portion of the projections 90. As the introducer 170 is moved in the direction of arrow 230 and engages the projections 90, the projections 90 may fold, is illustrated in FIG. 6, to be generally aligned or extended over or past the terminal end 152 of the catheter. Accordingly, as the introducer 170 unfolds or removes the projections 90 from being in contact or near a wall of the ventricle 34 may be collected or positioned within the introducer 170, is illustrated in FIG. 4.

The introducer 170 may, therefore, continue to be moved generally in the direction of arrow 230. At a selected point, such as a position of the projections 90 relative to the catheter 14, the catheter 14 may also be moved generally in the direction of arrow 238. The projections 90 may, therefore, be maintained within the introducer 170 as it is withdrawn from the subject 40. The spacer 82 including the projections 90 may then be removed from the subject 40 through the introducer 170.

Further, as illustrated in FIG. 6, the introducer 170 may be positioned at a selected location relative to the catheter 14. The catheter 14 may then be moved generally in the direction of arrow 238 to move the projections 90 into contact with the terminal end 190 of the introducer 70. In this manner, the introducer 230 may generally not move in the direction of arrow 230 to cause collapse or folding of the projections 90 into the introducer 170. Rather movement of the catheter 14 generally in the direction of arrow 238 may move the spacing member 82 also generally in the direction of arrow 238 to cause the projections 90 contact the terminal end 190 and fold into the interior of the introducer 170.

Accordingly, the catheter 14 may be removed from the subject 40 by either movement of the introducer 170 generally in the direction of arrow 230 to fold or collapse the projections 90. In addition and/or alternatively thereto, the catheter 14 may be moved generally in the direction of arrow 238 to collapse the projections 90 into the introducer 170. Regardless, the relative movement of the projections 90 relative to the introducer 170 may cause the projections 90 to move away from the catheter 34 and allow for an efficient removal or revision of the catheter 14 from the ventricle 34 and/or the subject 14.

As discussed above, therefore, the catheter 14 including the spacer member 82 may be positioned and/or removed from the subject 40. The spacer member 82 may assist in positioning or ensuring the positioning of the internal wall 34*w* at a distance from the through-bores 70. The spacer member 82, therefore, provides a barrier to contact with the through-bores 70 such as from the wall 34*w*. The spacing of the internal wall 34*w* from the through-bores 70 may assist in ensuring maintaining flow through the through-bores 70, such as in a selected manner. The space may further assist in ensuring or resisting in growth of tissue into the through-bores over the through-bores 70 of the catheter 14.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A shunt assembly for a subject to shunt fluid from a first location to a second location, comprising:

an inlet catheter having a wall defining an external surface and an internal surface and extending from a proximal end to a distal terminal end;

an internal passage defined by the internal surface and extending from the proximal end to the distal terminal end of the inlet catheter to shunt fluid from the first location to the second location;

a through-bore formed through the wall from the external surface to the internal passage to receive the fluid; and
a spacer member immovably fixed relative to the external surface of the wall and having a projection configured to be moved between a first position to position tissue away from the through-bore and a second position extending past the distal terminal end of the inlet catheter;
wherein when the projection is in the first position a distal end of the projection is angled radially toward the wall and extends to a plane to overlay relative to the through-bore and position the projection proximal the distal terminal end of the inlet catheter.

2. The shunt assembly of claim 1, wherein the spacer is formed of elastically deformable material operable to elastically return to a selected configuration after a deformation from the selected configuration.

3. The shunt assembly of claim 1, wherein the spacer member is formed of a shape memory alloy.

4. The shunt assembly of claim 1, wherein the spacer member includes a fixation portion configured to fix the spacer member to the wall of the inlet catheter;
wherein the projection extends from the fixation portion.

5. The shunt assembly of claim 4, wherein the projection includes (i) a first portion that is curved and is connected to the fixation portion and (ii) a second substantially straight or planar portion extending from the curved portion.

6. The shunt assembly of claim 5, wherein the first portion extends radially away from the wall and the second portion extends from the curved portion and radially towards the wall where the distal end of the projection is directed at the angle toward the wall.

7. The shunt assembly of claim 1, further comprising:
an outlet catheter; and
a flow regulator;
wherein both the inlet catheter and the outlet catheter are connected to the flow regulator.

8. The shunt assembly of claim 7, wherein the inlet catheter, the flow regulator, and the outlet catheter are configured to allow the fluid to flow from the inlet catheter to the outlet catheter.

9. The shunt assembly of claim 1, wherein when the projection is in the second position, the distal end of the projection is directed distally away from the distal terminal end of the inlet catheter.

10. A shunt assembly for a subject to shunt fluid from a first location to a second location, comprising:
an inlet catheter having a catheter wall defining an external surface and an internal surface and extending from a proximal end to a distal terminal end;
an internal passage defined by the internal surface and extending from the proximal end to the distal terminal end of the inlet catheter to shunt fluid from the first location to the second location;
a through-bore formed through the catheter wall from the external surface to the internal passage to receive the fluid;
a spacer member having (i) a fixation portion immovably fixed to the catheter wall and (ii) a projection extending from the fixation portion and configured to be moved between a first position to position tissue away from the through-bore and a second position extending past the distal terminal end of the inlet catheter; and
a depression in the external surface of the wall of the inlet catheter;
wherein the fixation portion is at least immovably positioned and fixed within the depression;
wherein the projection includes (i) a first portion that is curved and is connected to the fixation portion and (ii) a second substantially straight or planar portion extending from the curved portion;
wherein the first portion extends radially away from the wall and the second portion extends from the curved portion and radially towards the wall where the distal end of the projection is directed at an angle toward the wall.

11. The shunt assembly of claim 10, wherein the through-bore includes a plurality of through-bores;
wherein the projection includes a plurality of projections extending from the fixation portion and over the plurality of through-bores.

12. The shunt assembly of claim 11, further comprising:
an introducer having an introducer wall defining an internal surface and having an introducer terminal end;
wherein the introducer terminal end is configured to contact the plurality of projections and extend the plurality of projections past the distal terminal end of the inlet catheter.

13. The shunt assembly of claim 12, further comprising:
an insertion member configured to engage the inlet catheter within the internal passage.

14. The shunt assembly of claim 10, further comprising:
an outlet catheter; and
a flow regulator;
wherein both the inlet catheter and the outlet catheter are connected to the flow regulator.

15. The shunt assembly of claim 10, wherein the depression in the external surface of the wall is an annular depression or groove having a depth.

16. The shunt assembly of claim 15, wherein the fixation portion is a ring having an external surface such that when the ring is positioned within the annular groove, the ring is substantially flush with the external surface of the inlet catheter.

17. A method of placing a shunt assembly within a subject to shunt fluid from a first location to a second location, comprising:
providing an inlet catheter having (i) a catheter wall defining an external surface and an internal surface and extending from a proximal end to a distal terminal end, (ii) an internal passage defined by the internal surface and extending from the proximal end to the distal terminal end of the inlet catheter, and (iii) a through-bore formed through the catheter wall from the external surface to the internal passage to shunt fluid from the first location to the second location; and
positioning a spacer member immovably fixed on the catheter wall having (i) a fixation portion immovably fixed to the catheter wall and (ii) a projection extending from the fixation portion and configured to be moved between a first position to position tissue away from the through-bore and a second position extending past the distal terminal end of the inlet catheter;
wherein when the projection is in the first position a distal end of the projection is angled radially toward the wall and extends to a plane to overlay relative to the through-bore and position the projection proximal the distal terminal end of the inlet catheter.

18. The method of claim 17, further comprising:
contacting the projection with an introducer terminal end of an introducer to extend the projection past the distal terminal end of the inlet catheter from a non-extended position.

19. The method of claim 18, further comprising:
moving the inlet catheter and the spacer member into the introducer.

20. The method of claim 19, further comprising:
positioning the introducer with the inlet catheter and spacer member therein within the subject.

21. The method of claim 19, further comprising:
withdrawing the introducer to allow the projection to return to the non-extended position where the distal end of the projection is planer and flat.

\* \* \* \* \*